United States Patent
Gardner

(10) Patent No.: US 7,309,857 B2
(45) Date of Patent: Dec. 18, 2007

(54) GAMMA RAY DETECTORS HAVING IMPROVED SIGNAL-TO-NOISE RATIO AND RELATED SYSTEMS AND METHODS FOR ANALYZING MATERIALS IN AN OIL WELL

(75) Inventor: Robin Pierce Gardner, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 276 days.

(21) Appl. No.: 10/820,632

(22) Filed: Apr. 8, 2004

(65) Prior Publication Data

US 2004/0256548 A1 Dec. 23, 2004

Related U.S. Application Data

(60) Provisional application No. 60/461,801, filed on Apr. 10, 2003.

(51) Int. Cl.
*G01V 5/12* (2006.01)
(52) U.S. Cl. ..................... 250/266; 250/269.3
(58) Field of Classification Search ................ 250/266, 250/269.3
See application file for complete search history.

(56) References Cited

U.S. PATENT DOCUMENTS

| | | | |
|---|---|---|---|
| 2,830,184 A | 4/1958 | Scherbatskoy | ................ 250/71 |
| 2,881,324 A | 4/1959 | Scherbatskoy | ................ 250/71 |
| 2,946,888 A | 7/1960 | Scherbatskoy | .............. 250/71.5 |
| 2,992,331 A | 7/1961 | Bonner et al. | ............. 250/71.5 |
| 3,041,454 A | 6/1962 | Jones et al. | ................. 250/71.5 |
| 3,041,455 A * | 6/1962 | Meyerhof | ................... 250/264 |
| 3,088,030 A | 4/1963 | Rickard | ...................... 250/71.5 |
| 3,626,187 A | 12/1971 | Laney | ......................... 250/362 |
| 3,654,464 A | 4/1972 | Johnson, Jr. et al. | ...... 250/71.5 |
| 4,251,724 A * | 2/1981 | Vagelatos et al. | ........... 250/264 |
| 4,384,205 A * | 5/1983 | Flaum | ........................ 250/265 |
| 4,582,992 A | 4/1986 | Atwell et al. | ............. 250/359.1 |
| 4,764,677 A * | 8/1988 | Spurney | ................. 250/361 R |
| 4,841,153 A | 6/1989 | Wormald | ............... 250/390.04 |

(Continued)

FOREIGN PATENT DOCUMENTS

GB 1 000 044 A 8/1965

(Continued)

OTHER PUBLICATIONS

Bartholomew et al., "The $^{199Hg\,(n,\,\gamma)\,200}$ Hg Reaction with Thermal Neutrons," *Canadian Journal of Physics* 45: 1517-1540 (1967).

(Continued)

*Primary Examiner*—David Porta
*Assistant Examiner*—David S Baker
(74) *Attorney, Agent, or Firm*—Myers Bigel Sibley & Sajovec

(57) ABSTRACT

A gamma ray detector assembly for placement in a logging tool in a borehole can include a first gamma ray detector elongated along an axis and having a void extending along the axis. A second gamma ray detector conforms to at least a portion of the void. The first and the second gamma ray detectors are configured to be positioned in the borehole.

21 Claims, 15 Drawing Sheets

U.S. PATENT DOCUMENTS

| | | | |
|---|---|---|---|
| 4,937,446 A * | 6/1990 | McKeon et al. | 250/269.7 |
| 5,023,449 A * | 6/1991 | Holenka et al. | 250/252.1 |
| 5,105,080 A * | 4/1992 | Stoller et al. | 250/269.7 |
| 5,390,115 A * | 2/1995 | Case et al. | 702/8 |
| 6,220,371 B1 * | 4/2001 | Sharma et al. | 175/50 |
| 6,747,270 B2 * | 6/2004 | Pereira et al. | 250/269.4 |
| 7,214,942 B2 * | 5/2007 | Gardner | 250/360.1 |
| 2004/0256566 A1 | 12/2004 | Gardner | 250/266 |
| 2007/0051892 A1 * | 3/2007 | Warburton et al. | 250/362 |
| 2007/0085014 A1 * | 4/2007 | McIntyre et al. | 250/367 |

FOREIGN PATENT DOCUMENTS

| | | |
|---|---|---|
| GB | 1000044 | 8/1965 |

OTHER PUBLICATIONS

Bartholomew et al., "Spins of Levels in $N^{15}$, $Fe^{57}$, $Cu^{64}$, $Zr^{92}$, and $Hg^{200}$ By Neutron Capture $\gamma$-Ray Directional Correlations," *Nuclear Physics* 50: 209-233 (1964).

Hoogenboom. A.M., "A New Method in Gamma-Ray Spectroscopy: A Two Crystal Scintillation Spectrometer with Improved Resolution," *Nuclear Instruments* 3: 57-68 (1958).

U.S. Appl. No. 10/820,633, R. P. Gardener, filed Apr. 8, 2004.

International Search Report for PCT/US2004/011665; Date of mailing Nov. 11, 2004.

Ember et al. "Improvement of the capabilities of PGAA by coincidence techniques", Applied Radiation and Isotopes 56:535-541 (2002).

Ember et al. "Coincidence measurement setup for PGAA and nuclear structure studies", Applied Radiation and Isotopes 57:573-577 (2002).

International Search Report for PCT/US2004/011666; Date of mailing Dec. 29, 2004.

Ember et al. "Coicidence Measurement Setup for PGAA and Nuclear Structure Studies" *Applied Radiation and Isotopes* 57(4): 573-577 (2002).

Ember et al. "Improvement of the Capabilities of PGAA by Coincidence Techniques" *Applied Radiation and Isotopes* 56(3): 535-541 (2002).

International Search Report and Written Opinion of the International Searching Authority for Application No. PCT/US2004/011666 mailed on Apr. 28, 2005.

Gardner et al., "A feasibility study of a coincidence counting approach for PGNAA applications", Applied Radiation and Isotopes 53 (2000) 515-526.

Gardner et al., "Practical Implementation of Coincidence Prompt Gamma-Ray Neutron Activation Analysis", Transactions of the American Nuclear Society, vol. 89, pp. 486-487, 2003.

Metwally et al., "Elemental PGNAA analysis using gamma-gamma coincidence counting with the library least squares approach," Nuclear Instruments and Methods in Physics Research B 213 (2004) 394-399.

Metwally et al., "Two-dimensional diagonal summing of coincidence spectra for bulk PGNAA applications," Nuclear Instruments and Methods in Physics Research A 525 (2004) 511-517.

Gardner et al., "Q-value Summing for Coincidence Prompt Gamma-Ray Neutron Activation Analysis," Transactions of the American Nuclear Society, vol. 91, pp. 881-882, 2004.

Gardner et al., A new NaI detector arrangement for efficient detection of high energy gamma-rays, Journal of Radioanalytical and Nuclear Chemistry, vol. 264, No. 1 (2005) 133-137.

Metwally et al. "Coincidence counting for PGNAA application: Is it the optimum method?" Journal of Radioanalytical and Nuclear Chemistry, vol. 265, No. 2 (2005) 309-314.

* cited by examiner

GAMMA RAY DETECTORS HAVING IMPROVED SIGNAL-TO-NOISE RATIO AND RELATED SYSTEMS AND METHODS FOR ANALYZING MATERIALS IN AN OIL WELL

RELATED APPLICATIONS

This application claims the benefit of priority to U.S. Provisional Application Ser. No. 60/461,801, entitled, "Gamma Ray Detectors Having Improved Signal to Noise Ratio And Related Systems And Methods" filed Apr. 10, 2003, the disclosure of which is hereby incorporated herein by reference in its entirety.

FIELD OF THE INVENTION

The present invention relates generally to the analysis of materials in an oil well using gamma rays, for example, from neutron activation and, more particularly, to detectors having improved signal-to-noise ratio for analysis of gamma rays and related methods.

BACKGROUND OF THE INVENTION

The composition of a material can be analyzed based on the characteristics of the gamma rays detected by a gamma ray detector. For example, elements typically emit gamma rays at certain characteristic energies when activated with a suitable source of neutrons during neutron activation. Prompt Gamma Neutron Activation Analysis (PGNAA) and Neutron Inelastic Scattering (NIS) techniques have been used for measuring elemental composition in bulk samples. These techniques can produce high energy or highly penetrating gamma rays, which can allow the analysis of large sample volumes.

These techniques have been used to analyze materials in the context of oil well logging. In particular, the carbon/oxygen ratio may provide information about the relative amounts of oil or water in the well. The logging tool generally includes a fast neutron source and a radiation detector spaced apart from the source. The fast neutrons originating from the source collide with formation elements. These collisions often result in the emission of inelastic gamma rays and, subsequently, the slowing down of the neutrons. Neutrons can also be slowed by elastic collisions with elements with small nuclei, such as hydrogen, carbon, and oxygen. Upon slowing down, the neutrons may be captured and another set of gamma rays may be emitted. The resulting gamma rays, either before or after neutron slowing, are detected by the radiation detectors and the resulting spectra are analyzed to obtain information about the elemental amounts in the formation. Carbon and oxygen generally emit gamma rays ranging from 4.44 to 6.13 MeV, which can result from the interaction of fast neutrons with these elements. Gamma rays ranging from 1.6 to 4.8 MeV can also be detected from carbon and oxygen as a result of the capture of primarily thermal neutrons by these elements.

The gamma ray detectors used in a logging tool are constrained in size because of the relatively small size of a borehole. The resulting spectrum may have a low signal-to-noise ratio, and therefore, the data may have poor statistical significance and be difficult to analyze.

SUMMARY OF THE INVENTION

According to embodiments of the present invention, a gamma ray detector assembly for placement in a logging tool in a borehole is provided. A first gamma ray detector is elongated along an axis and defines a void extending along the axis. A second gamma ray detector conforms to at least a portion of the void. The first and the second gamma ray detectors are configured to be positioned in the borehole.

In some embodiments, the first and second gamma ray detector are cylindrical. The first gamma ray detector forms an outer cylinder and the second gamma ray detector forms an inner cylinder. The first gamma ray detector can have a thickness that varies around the perimeter of the second gamma ray detector. In some embodiments, the thickness is uniform.

In certain embodiments, a shielding material is positioned on an end of the first gamma ray detector, and a radioactive neutron source is positioned on a side of the shielding material facing away from the first gamma ray detector. The radioactive source is configured to irradiate material in a borehole. The detector assembly may further include a first photomultiplier tube in communication with the first gamma ray detector and a second photomultiplier tube in communication with the second gamma ray detector.

In particular embodiments, a signal processor is configured to receive signals from the first and second gamma ray detectors. The signal processor can be configured to detect a first event in one of the first and the second gamma ray detectors and to determine if a second event is detected in coincidence with the first event in the other of the first and the second gamma ray detectors. The signal processor can be configured to determine the rate of coincidence between an event in one of the first and second detectors and an annihilation photon in the other of the first and second detectors, the rate of coincidence between an event and two annihilation photons, and the rate of coincidence between a first event and a second event, wherein the first event and the second event sum to a predetermined energy. The predetermined energy can be between about 1.5 MeV to about 11 MeV. In some embodiments, the signal processor is configured to determine a ratio of oxygen and carbon based on events in the first and second gamma ray detectors.

According to method embodiments of the present invention, methods of detecting coincidence in gamma ray detectors in a borehole are provided. A first gamma ray detector and a second gamma ray detector are placed into a borehole. The first and second gamma ray detectors can be configured as described above. A first event is detected in one of the first gamma ray detector and/or the second gamma ray detectors. It is determined whether a second event is detected in coincidence with the first event in the other of the first and the second gamma ray detectors.

Coincidence counting techniques according to embodiments of the present invention may be made of entirely hardware, entirely software, or a combination of hardware and software embodiments.

DETAILED DESCRIPTION OF EMBODIMENTS OF THE INVENTION

Figure 1:
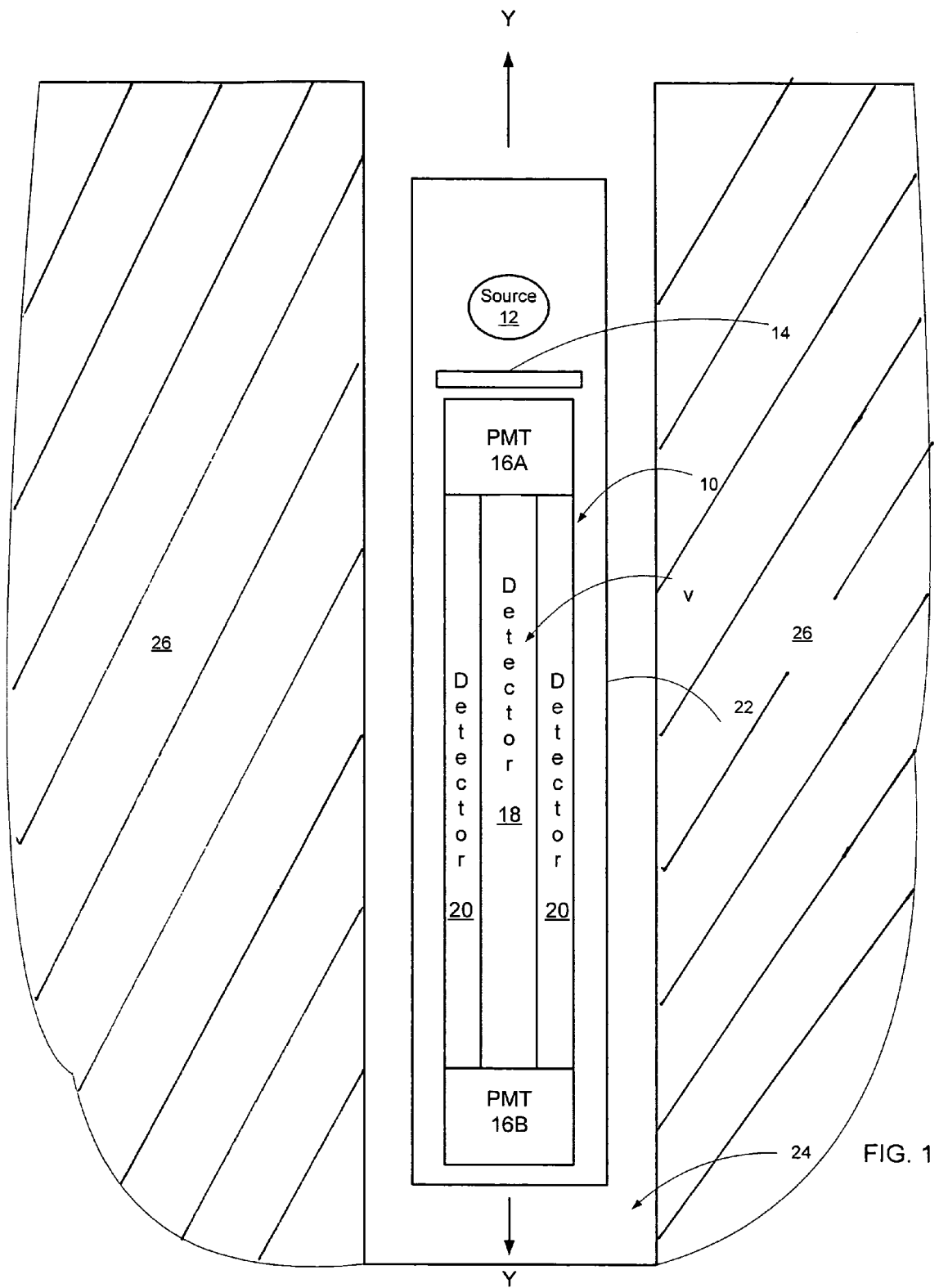
FIG. 1 is a schematic diagram of a gamma ray detector assembly according to embodiments of the present invention placed in a borehole of an oil well.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements throughout. Thicknesses and dimensions of some components may not be drawn to scale and may be exaggerated for clarity. It will be understood that when an element is referred to as being "on" or "adjacent" another element, it can be directly on or adjacent the other element or intervening elements may also be present. In contrast, when an element is referred to as being "directly on" another element, there are no intervening elements present.

As used herein, the term "event" refers to the detection of a gamma ray or gamma ray interaction. Two or more events may be caused by the same gamma ray.

A detector assembly 10 according to embodiments of the present invention is shown in FIG. 1. The detector assembly 10 includes detectors 18, 20 and photomultiplier tubes 16A, 16B. The detector assembly 10 is separated from a source 12 by a shielding material 14 such as lead. As illustrated, the source 12, shielding material 14, photomultiplier tubes 16A, 16B and detectors 20 are enclosed in a housing 22. Scintillation photons from detector 18 are received by photomultiplier tube 16A and scintillation photons from detector 20 are received by photomultiplier tube 16B to provide a signal indicating the detection of gamma ray events. The detectors 18, 20 and the photomultiplier tubes 16A, 16B can form an integrated detector device and the detectors 18, 20 can be in contacting relationship with one another or the detectors 18, 20 can be separated by a small space. The housing 22 is a substantially waterproof housing or logging tool that is designed for use in the borehole of an oil well, which may expose the detector assembly 10 to water and other fluids and high temperatures and/or high pressure conditions. Examples of logging tools used in a borehole environment are discussed in U.S. Pat. No. 4,760,252 to Albats et al., the disclosure of which is incorporated herein by reference in its entirety. Although the detectors 18, 20 and photomultiplier tubes 16A, 16B are shown with respect to the housing 22, other configurations can be used. For example, the detectors 18, 20 and photomultiplier tubes 16A, 16B can be integrated as part of other oil well logging devices, such as devices for measuring the gamma density, natural gamma rays, and/or the neutron porosity.

The detector assembly 10 and the housing 22 are configured so that it can be placed in a borehole 24. As illustrated, the detector 20 is elongated along axis Y-Y and has a void V that extends along the axis Y-Y. The detector 18 is adapted to conform to the void V. In this configuration, the detectors 18, 20 are configured to be positioned in a borehole logging tool, which is generally cylindrical with an outer diameter of about three to six inches and a length as long as about thirty feet. For example, the detectors can be sized to fit into a circular borehole, such as a borehole for an oil well. However, the detectors can be sized to fit into other types of boreholes. For example, boreholes in an oil well are typically between about six and about ten in diameter, and the logging tools are generally smaller than the borehole diameter. These boreholes may be several miles in depth. In some embodiments, the detector assembly 10 has a generally cylindrical shape with an outside diameter of about 1-and-⅞ inch and a length from about six to about twelve inches. As illustrated, the detectors 18, 20 and the detector assembly 10 are elongated, i.e., having more length than width. For example, the detector assembly 10 can have a length to width ratio of between about 1.5 to about 4 or 5 or more.

The detector assembly 10 can be used to analyze the composition of surrounding materials 26. The detector assembly 10 can be mounted within an oil well logging device to facilitate the analysis of the surrounding materials 26. Data from the detector assembly 10 can be analyzed, for example, to determine the carbon/oxygen ratio of the surrounding materials 26. The carbon/oxygen ratio can be used as an indication of how much oil or water is present in the surrounding materials 26.

In this configuration, gamma rays from neutron activation can be used to analyze material in an oil well. Embodiments of the present invention can incorporate coincidence-counting techniques that may improve the signal-to-noise ratio and reduce background in a dataset or spectrum. The effects of summing and pulse pile up may also be reduced. "Summing" and "pulse pile up" refer to coincidence events that are detected at approximately the same time in one detector. This results in a single higher energy event being recorded rather than two lower energy events. Summing is generally the result of gamma rays emitted from a source at the same time in true coincidence. Pulse pile up generally refers to random coincidence events from more than one source that randomly occur at the same time.

The source 12 can be a neutron source that emits neutrons. In some embodiments, the source 12 is a fast neutron source such as an accelerator source that produces neutrons with an energy of about 14 MeV. Examples of other neutron sources include Cf-252, Am-241-Be, and radium/beryllium sources. Neutrons from the source 12 undergo collisions with the surrounding materials 26. Without wishing to be bound by theory, these collisions may result in the emission of inelastic gamma rays and, subsequently, the slowing down of the neutrons. Upon slowing down, the neutrons may be captured, which may cause the emission of still more gamma rays. The gamma rays from these and other reactions may be detected by the detectors 18, 20 combined with the photomultiplier tubes 16A, 16B. For example, the detector assembly 10 may include light insulating layers to isolate the detectors 18 from the photomultiplier tube 16B and to isolate the detector 20 from the photomultiplier tube 16A. In this configuration, scintillation photons from the detector 18 are received by the photomultiplier tube 16A and scintillation photons from the detector 20 are received by the photomultiplier tube 16B. Gamma rays can pass through the outside detector 20 and into the inner detector 18. A material such as wax (not shown) may also be incorporated into the configuration shown in FIG. 1 in order to thermalize neutrons from the source 12.

Gamma rays are generally detected when an incident gamma ray interacts with matter in a detector. A single gamma ray may result in multiple interactions or "events" in detectors 18, 20. When more than one event occurs as the direct or indirect result of a single gamma ray in detectors 18, 20, the timing of the events may indicate the relationship of the events to a single gamma ray. Such events may be detected in "coincidence." That is, when two or more events occur within a certain time range, typically between about 10 and about 100 nanoseconds (or less), the events can be defined as being in coincidence. For example, and again without wishing to be bound by theory, when an incident gamma ray undergoes an interaction in the inside detector 18, a pair production interaction may occur. This interaction can deposit all of the gamma ray energy minus 1.022 MeV at the interaction site and produce two 0.511 MeV annihilation photons that are emitted in opposite directions. In such a reaction in the inside detector 18, at least one of the 0.511 MeV annihilation photons may be detected in the outside detector 20 in coincidence with the deposition of energy in the inside detector 18. Such pair production reactions may be more likely to occur as the incident gamma ray energy increases.

Any suitable detector can be used for the detectors 18, 20. For example, detectors 18, 20 may be scintillating radiation detectors such as scintillating detectors including crystals such as NaI(T1), LSO, BGO, KBr(T1), NaBr(T1), KI(T1), KCl(T1), CsI(Na), CsI(T1) or polyvinyl toluene plastic scintillators. Scintillating radiation detectors typically utilize a photomultiplier tube to detect scintillation and amplify the resulting signal. The detectors 18, 20 may also be semiconductor detectors such as germanium or gallium nitride detectors. However, gallium nitride detectors normally have to be kept cooler than scintillation detectors. Such detectors may not require photomultiplier tubes 16A, 16B, and therefore, the photomultiplier tubes 16A, 16B may be omitted. In other embodiments, both detectors are scintillation detectors. Scintillation detectors may withstand the temperature conditions in an oil well borehole.

Figure 2A:
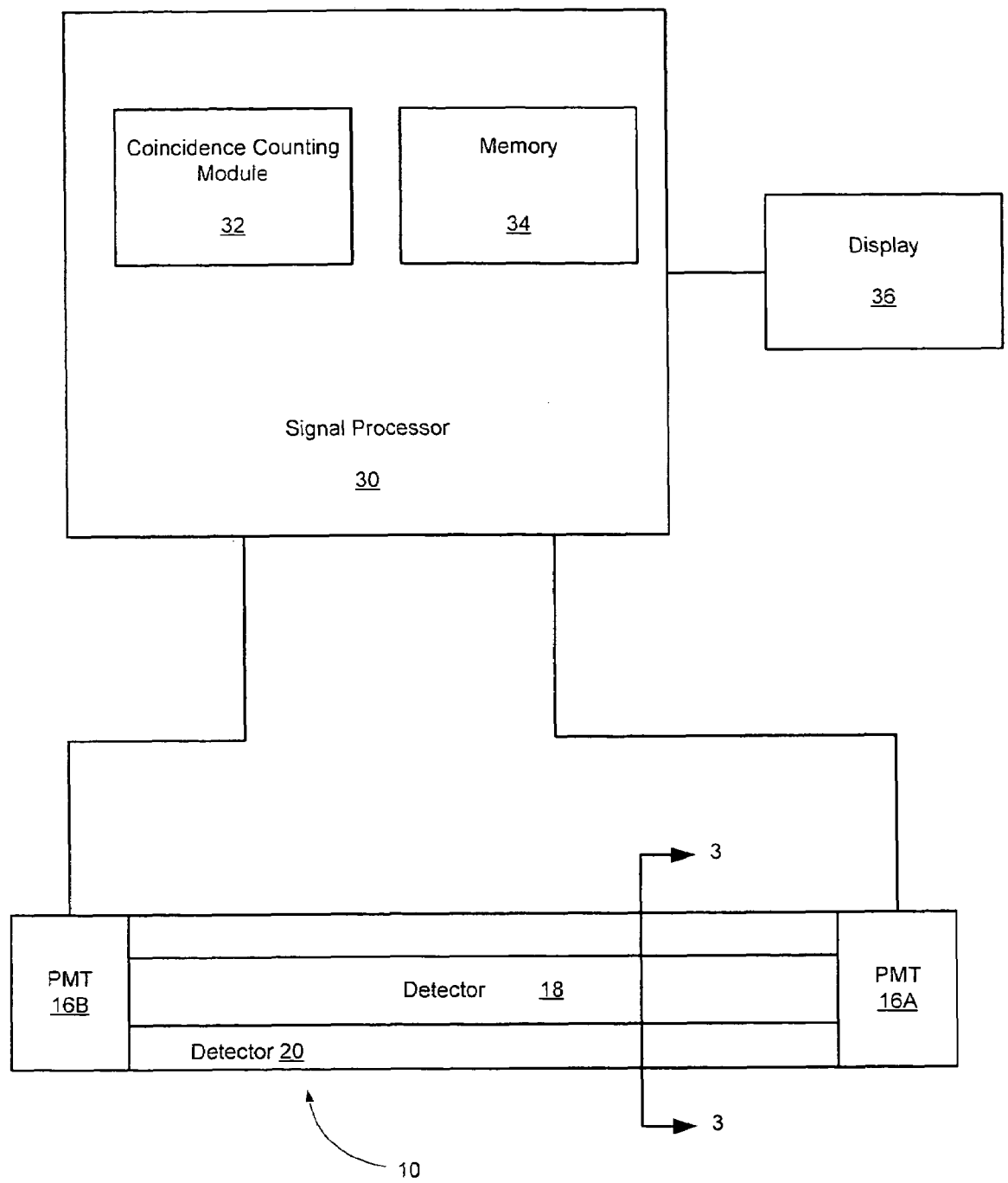
FIG. 2A is a schematic diagram of the gamma ray detector assembly of FIG. 1 and a signal processor according to embodiments of the present invention.
Figure 3:
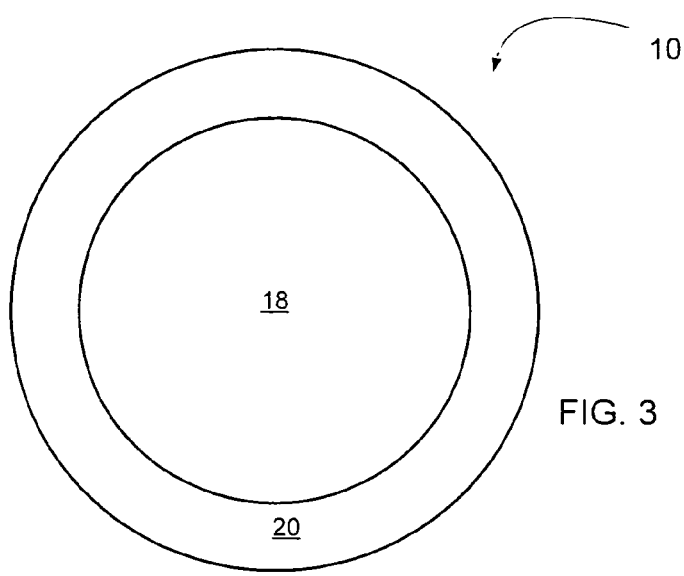
FIG. 3 is a cross sectional view of the gamma ray detector assembly of FIGS. 1 and 2A taken along the line 3-3 of FIG. 2A.

FIG. 2A illustrates the detector assembly 10 from FIG. 1 in communication with a signal processor 30. FIG. 3 is a cross-section of the detectors, 18, 20 taken along line 3-3 in FIG. 2A. The photomultiplier tubes 16A, 16B amplify a signal from the gamma ray detectors 18, 20 and transfer the signal to the signal processor 30. The signal processor 30 includes a coincidence counting module 32 and a memory 34. The signal processor 30 is connected to a display 36.

As illustrated in FIG. 3, the detector 20 extends around the detector 18. The detector 18 can be described as a cylinder that fits inside detector 20. In some embodiments, the detector 18 is about one inch in diameter.

As illustrated in FIG. 2A, signals that indicate events in the scintillation detectors 18, 20 are processed by the signal processor 30. The coincidence counting module 32 can determine a coincidence counting rate by identifying events that are in coincidence, and coincidence and/or non-coincidence events can be recorded or stored in the memory 34. The signals and/or events from the detectors 18, 20 can be stored in the memory 34 and processed at a later time. The signals can also be processed as they are received from the detector assembly 10 and subsequently stored in the memory 34.

The coincidence counting module 32 can carry out operations according to embodiments of the present invention. For example, the coincidence counting module 32 can read data from the memory 34 or from the detector assembly 10 in order to determine if events are coincidence events or if an event is a single event that is not in coincidence with other events. Although the coincidence counting module 32 is illustrated with respect to the processor 30, other configurations can be used to carry out operations according to embodiments of the present invention. For example, the coincidence counting module 32 and/or the processor 30 can be incorporated into the detector assembly 10 or the coincidence counting module 32 may be incorporated into the memory 34.

The display 36 may display raw data and/or data that has been processed or selected by the signal processor 30. The display 36 may be part of the signal processor 30 or the display 36 can be a separate device. Data can be displayed by the display 36 in real time as the data is being collected, or it can be stored in the memory 34 and displayed at a later time. In some embodiments, the display 36 and/or memory 34 is omitted.

Figure 2B:
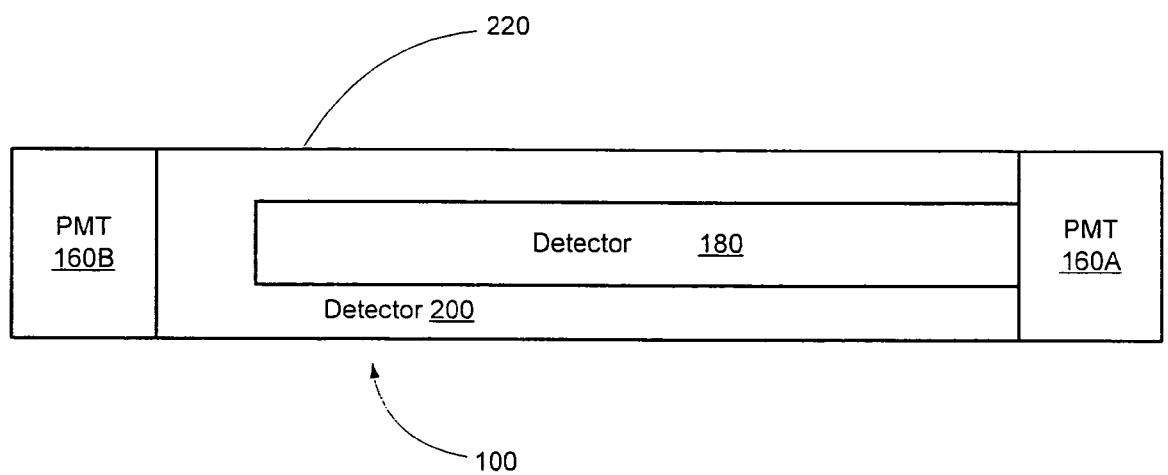
FIG. 2B is a schematic diagram of a gamma ray detector according to further embodiments of the present invention.

Other configurations of "inner" and "outer" detectors can be used such that the outer detector defines a void and the inner detector is configured to conform to at least a portion of the void. For example, the void can be a passageway with two open ends, a cavity with one open end, or a void entirely surrounded by the outer detector on all sides. A detector assembly 100 according to further embodiments of the present invention is shown in FIG. 2B. The detector assembly 100 includes an inner detector 180 and an outer detector 200 relatively configured such that the inner detector 180 does not extend the entire length of the outer detector 200. The detector 180 is in communication with the photomultiplier tube 160A and the detector 200 is in communication with the photomultiplier tube 160B. The detector assembly 100 can be positioned in a borehole, for example, as shown with respect to the detector assembly 10 in FIG. 1. As illustrated in FIG. 2B, the photomultiplier tubes 160A, 160B and the detectors 200 are enclosed in a housing 220.

Although the detector assemblies 10, 100 are described herein as generally cylindrical, other shapes can be used. For example, other cross-sectional shapes can be used such as ovals, rectangles, squares and the like.

Figure 4:
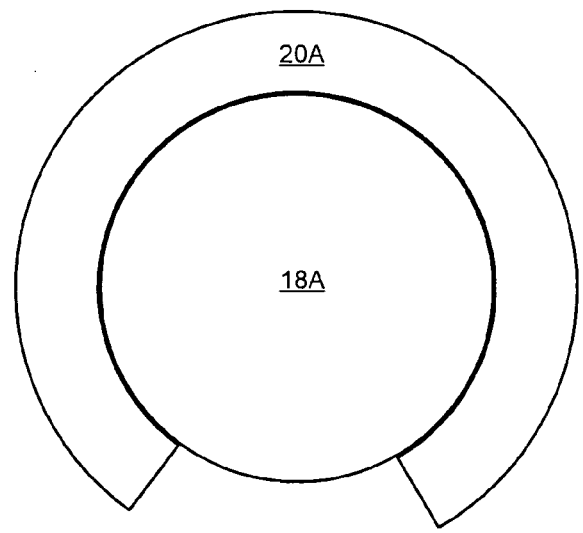
FIG. 4 is a cross sectional view of a gamma ray detector assembly according to further embodiments of the present invention.
Figure 5:
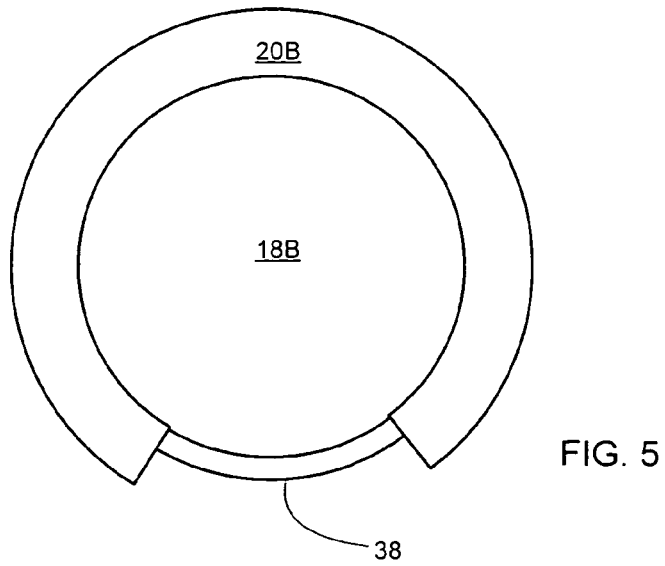
FIG. 5 is a cross sectional view of a gamma ray detector assembly according to still further embodiments of the present invention.

Further examples of alternative detector arrangements are shown in FIGS. 4 and 5. FIG. 4 illustrates an outside detector 20A that extends around a portion of inside detector 18A. As shown in FIG. 5, an outside detector 20B extends around an inside detector 18B. The outside detector 20B has a reduced thickness at a portion 38. The portion 38 can be integrated with the outside detector 20B or provided as a separate detector piece.

Other detector configurations may be used. For example, three or more detectors may be combined in a detector assembly and coincidence events in two or more detectors can be identified.

Figure 6:
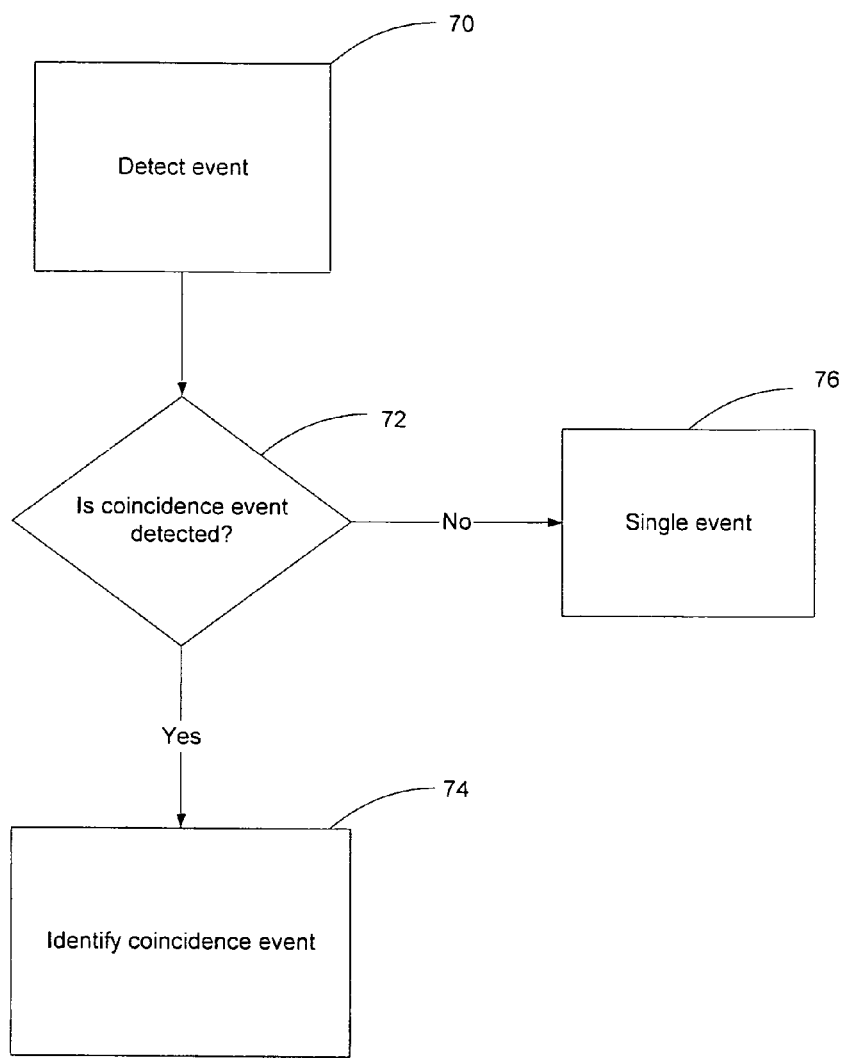
FIG. 6 is a flow chart illustrating operations according to embodiments of the present invention.

Operations according to embodiments of the present invention are shown in FIG. 6. Such operations may be carried out, for example, by the coincidence counting module 32. An event is detected (Block 70), for example, by the detector assembly 10 (FIGS. 1 and 2A) or the detector assembly 100 (FIG. 2B). If an event is detected as a coincidence event (Block 72), the event or events are identified as a coincidence events (Block 74). These events can be included in a coincidence dataset. If a coincidence event is not detected (Block 72), then the event is a single event (Block 76). Single events can be stored in memory (such as memory 34 in FIG. 1) and/or displayed. Alternatively, single events may be discarded from the dataset.

Various coincidence counting techniques and/or parameters for counting coincidence events may be used. Examples of coincidence counting parameters include the total coincidence, coincidence between any event and an annihilation photon event, and coincidence between events that sum to a predetermined energy. However, any subset of events in one detector can be selected and events that are in coincidence with the selected subset can be identified. The total coincidence between two detectors includes all events in one detector that are in coincidence with the other detector. Coincidence between any event and an annihilation photon includes events in one detector that are in coincidence with an annihilation photon in the other detector. Annihilation photons are produced when a positron annihilates, producing two 0.511 MeV photons. Coincidence summing to a predetermined energy include events in one detector that are in coincidence with events in another detector only if the energy of the two events sum to a predetermined energy level. Typical energy ranges are between and about 0.5 and about 11 MeV for the configuration shown in FIGS. 1 and 2A-B. For example, gamma ray energies from carbon and oxygen are 4.44 MeV and 6.13 MeV, respectively. Depending on detector resolution, these peaks may be detected in various energy ranges. For example, the carbon 4.44 MeV peak is typically detected in a range between about 4.2 and about 4.6 MeV for a NaI detector and between about 4.35 and 4.45 in a Ge detector due to increased resolution in a Ge detector. The 6.13 MeV oxygen peak is typically detected in a range between about 5.9 MeV and about 6.3 MeV in a NaI detector and between about 6.05 MeV and about 6.2 MeV in a Ge detector.

In certain embodiments, an outside "well" detector, such as detector 18 in FIG. 1, can have an outside diameter of about 1-and-7/8 inches and a length from about 2 to about 6 inches. The outside well detector can have a void or "well" with a diameter of about one inch. The inside "well-filling" detector, such as detector 20 in FIG. 1, can be configured to fill the inside of the one inch diameter well. These two detectors can be operated in coincidence so that only those detector pulses that occur simultaneously or within a certain time range are recorded or identified as being in coincidence. For example, these techniques may be used to detect relatively high gamma ray energies from carbon and oxygen, which are of interest in oil well logging operations. The energies of gamma rays from carbon and oxygen are 4.44 MeV and 6.13 MeV, respectively. Gamma rays produced by other elements and/or at other energy levels may also be detected. For example, the detection of silicon and calcium gamma rays may also be performed. Primary interactions of these gamma rays may be pair production reactions. There is a relatively high probability that one or both of the annihilation photons produced in pair production will be detected in the outer "well" detector if the initial interaction is in the inner well-filling detector. The initial interaction may deposit an energy equal to the full gamma ray energy minus 1.022 MeV or 0.511 MeV at the interaction site. These peaks may be called first and second "escape peaks." These events may occur at approximately the same time or within a selected time frame. Therefore, coincidence counting of these events (e.g., an escape and one or two 0.511 MeV photon interactions) may record these energies with reduced noise.

A coincidence device such as a Sparrow™ system (commercially available from Sparrow Corporation in Port Orange, Fla., U.S.A.) may be used that is capable of recording individual spectral counting rates from each detector while also recording the coincidence counting rates that occur at specific energies from each detector. This latter data may include three-dimensional data and provide the counts or counting rate as a function of the energy deposited in one detector that is in coincidence with energy deposited in a second detector at substantially the same time or within a specified time frame. From this three-dimensional data (counts as a function of energy in both detectors), those pulses that satisfy a predetermined coincidence criteria, such as adding to a prescribed energy, can be extracted. For example, either the carbon gamma ray energy (4.44 MeV) or the oxygen gamma ray energy (6.13 MeV) can be used. This can be used to produce a spectra that contains, for example, substantially only the first and second escape peaks of the carbon and/or oxygen energies along with the 0.511 MeV and the 1.022 MeV peaks. This may result in an improved spectrum with reduced noise. The reduction of signal due to coincidence counting may be relatively small.

Embodiments of the present invention will now be described with respect to the following non-limiting examples.

EXAMPLE 1

Sodium-24 Study

A $^{24}$Na radioactive gamma ray source was placed adjacent the detector assembly 100 shown in FIG. 2B. $^{24}$Na decays by emitting two well separated gamma rays of energies 1.368 and 2.754 MeV. Both of these gamma ray energies are above the threshold (1.02 MeV) of the pair production effect. Portions of the data obtained are illustrated in FIGS. 7-13.

Figure 7:
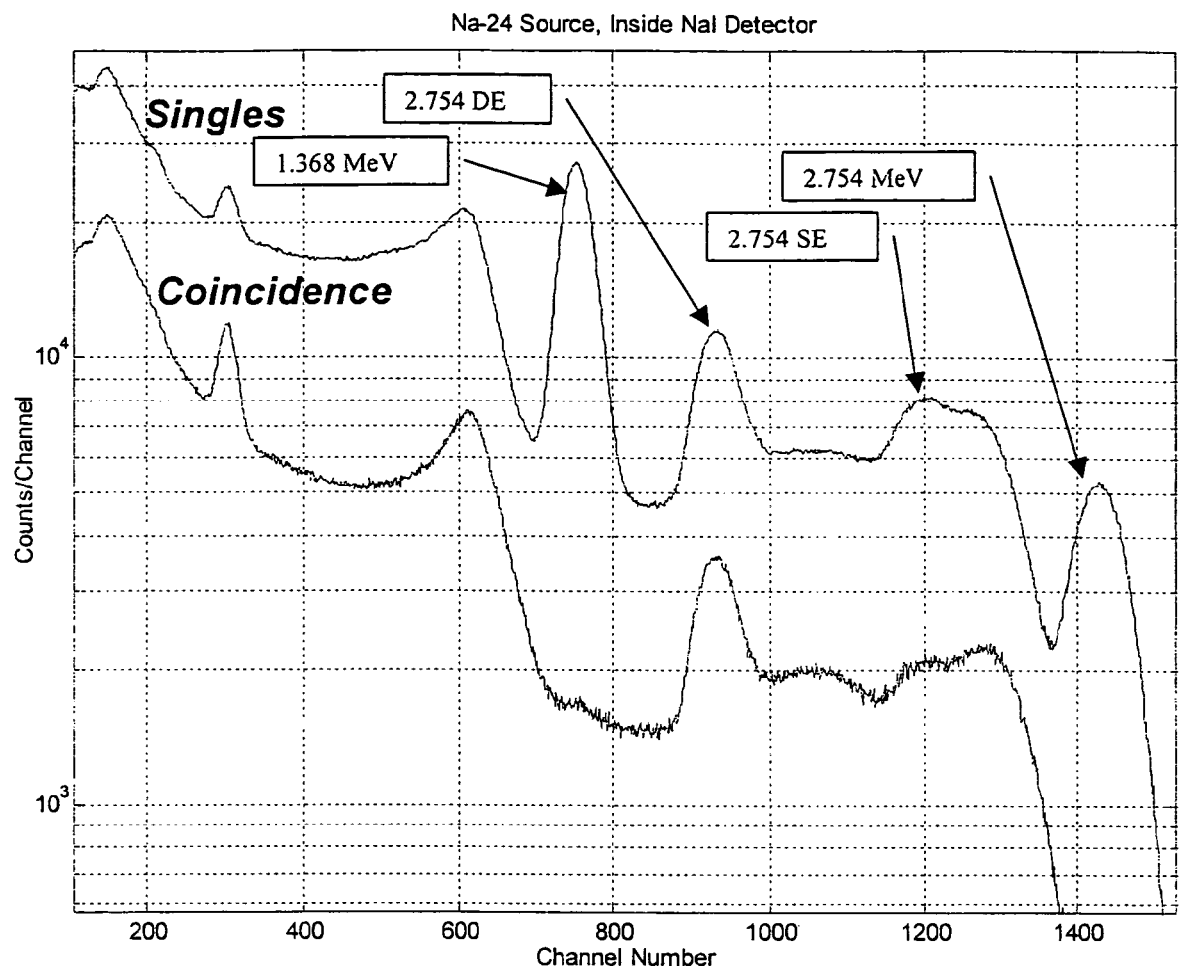
FIG. 7 is a graph illustrating a single events spectrum and a coincidence spectrum for a $^{24}$Na sample for an inner detector according to embodiments of the present invention.

The $^{24}$Na source was placed approximately 10 cm away from the center of the detectors to simulate radiation incident on the sides of the detectors as may be obtained in oil well logging applications. Because $^{24}$Na is radioactive, a neutron source was not required or used. FIG. 7 shows the obtained singles and total coincidence spectra.

As can be seen in FIG. 7, the total coincidence spectrum is approximately 2-3 times lower than the singles spectrum. The effects of summing and pulse pile up can be reduced. This may provide a higher detection sensitivity.

In some embodiments, information may be reduced using coincidence spectra because the coincidence spectra illustrate the detection of events related to only one gamma ray in coincidence. Thus, the full energy peak can be lost and numerous energy combinations that sum to the full energy peak may be obtained.

Figure 8:
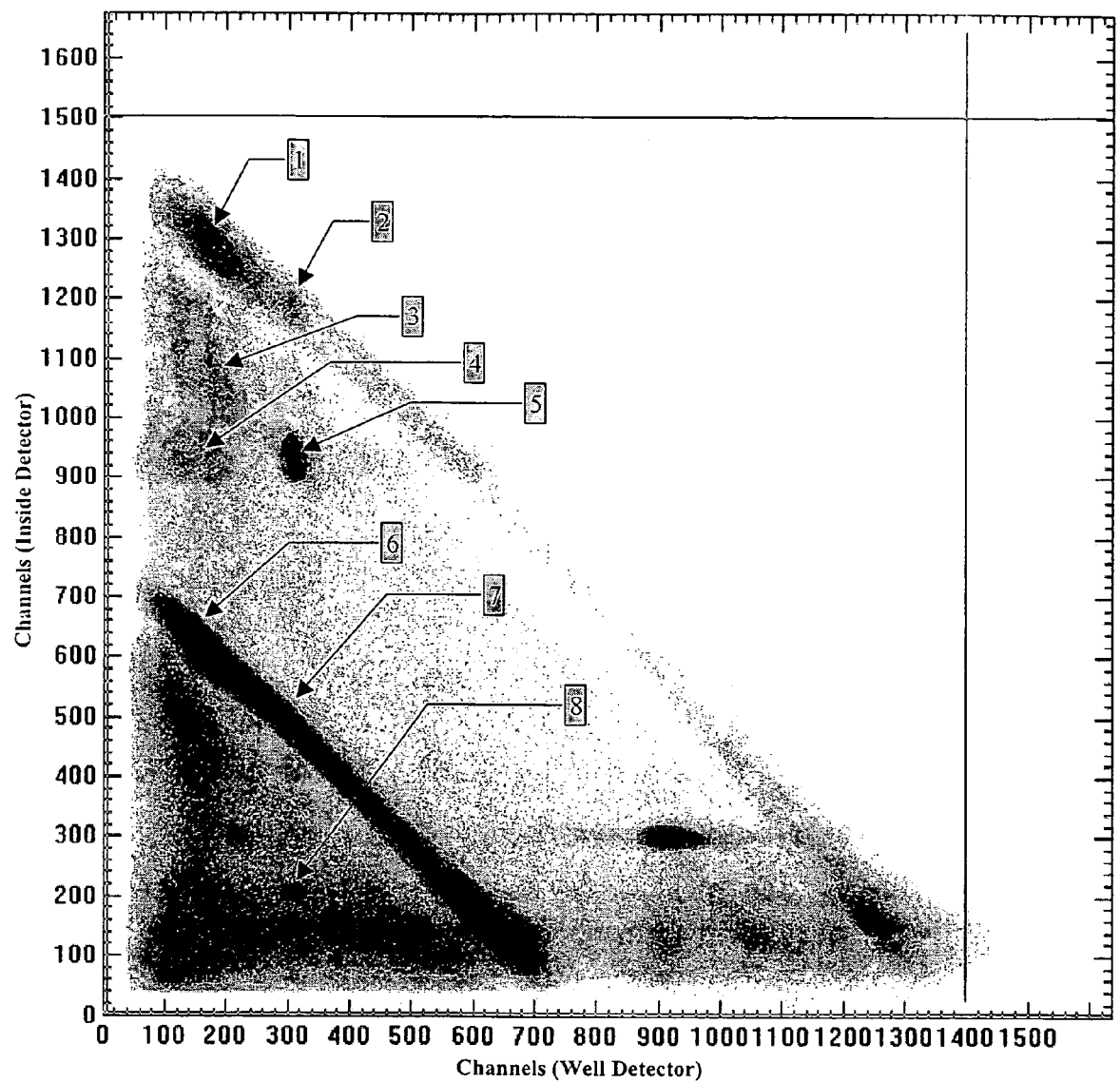
FIG. 8 is a graph of a two-dimensional representation of a three-dimensional spectrum for an inner and an outer detector for a $^{24}$Na gamma ray source according to embodiments of the present invention.
Figure 9:
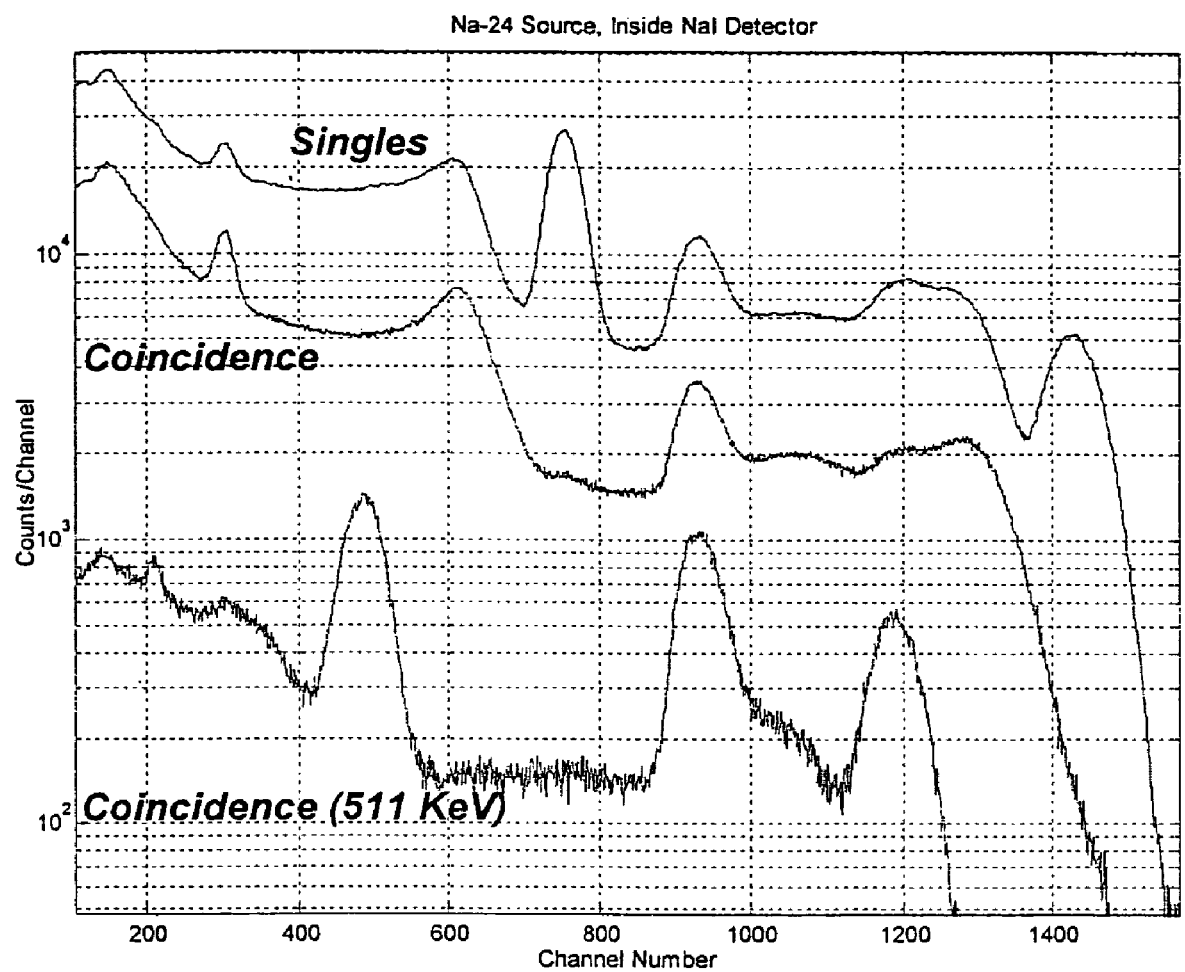
FIG. 9 is a graph illustrating a single events spectrum, a total coincidence spectrum, and a 0.511 MeV coincidence spectrum for a $^{24}$Na gamma ray source using an inner detector according to embodiments of the present invention.

FIG. 8 shows the two-dimensional spectrum obtained when using the $^{24}$Na source. Certain features are labeled on FIG. 8 and described in Table 1.

coincidence spectra are shown together in FIG. 9. It can be seen that the escape peaks of the 2.754 MeV and 1.368 MeV gamma rays appear with a high signal-to-noise ratio. The 0.511 MeV coincidence spectrum is almost an order of magnitude less than the single event spectrum.

Figure 10:
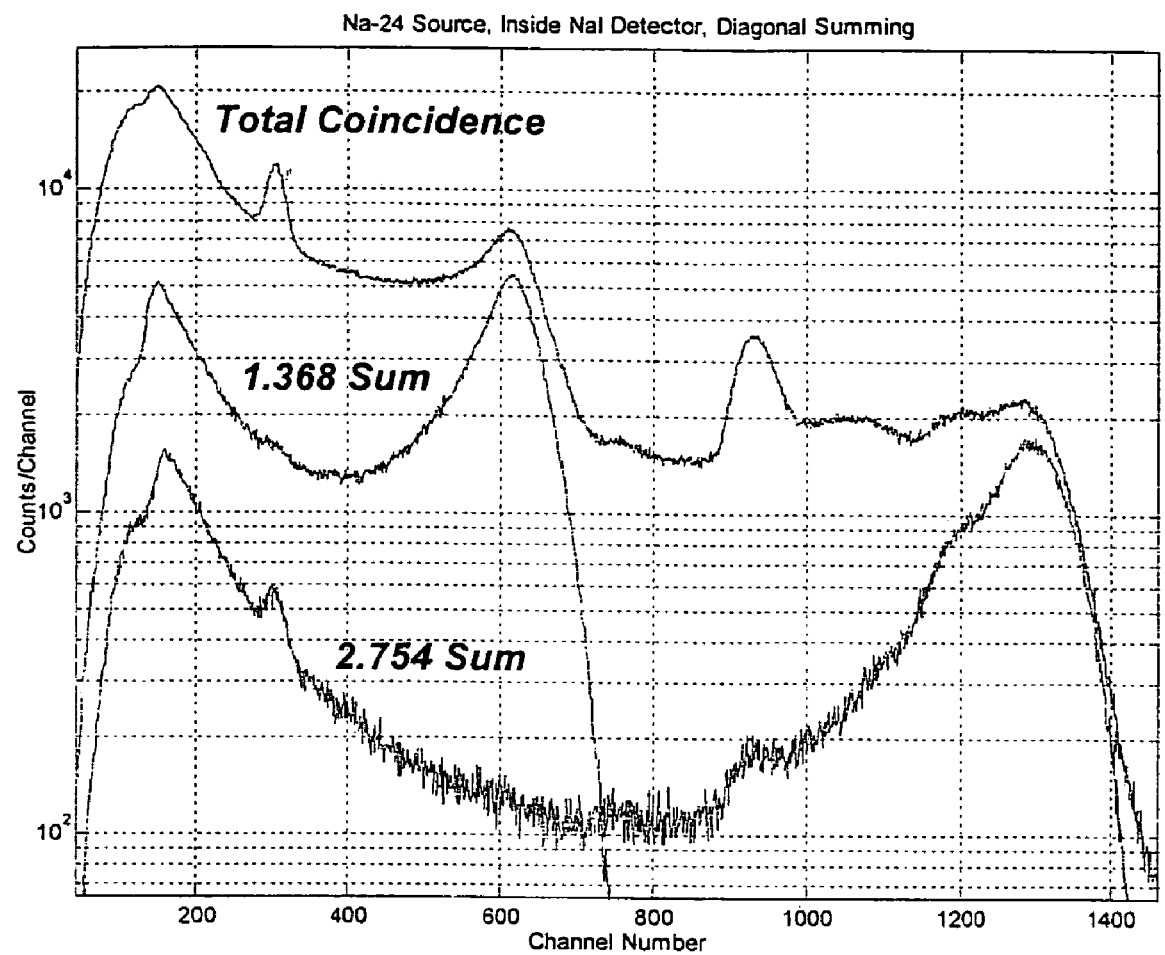
FIG. 10 is a graph illustrating a total coincidence spectrum, a coincidence summation spectrum at 1.368 MeV, and a coincidence summation spectrum at 2.754 MeV for a $^{24}$Na gamma ray source using diagonal summing techniques for an inner detector corresponding to the full energies of 1.368 MeV and 2.754 MeV according to embodiments of the present invention.

FIG. 10 shows the two diagonal summing spectra corresponding to the full energies of the 1.368 MeV and 2.754 MeV gamma rays. The shape of the spectra can be described by the comments on the first and second features in Table 1. Although there are no distinct peaks in the spectra presented in FIG. 10, one can still make use of this "V-shaped" data. This data may be analyzed using a Library Least Squares (LLS) analysis because of its well-defined characteristic shape. The data shown in FIG. 9 is almost the same intensity as the total coincidence on the right hand (high energy) side of the spectrum.

Figure 11:
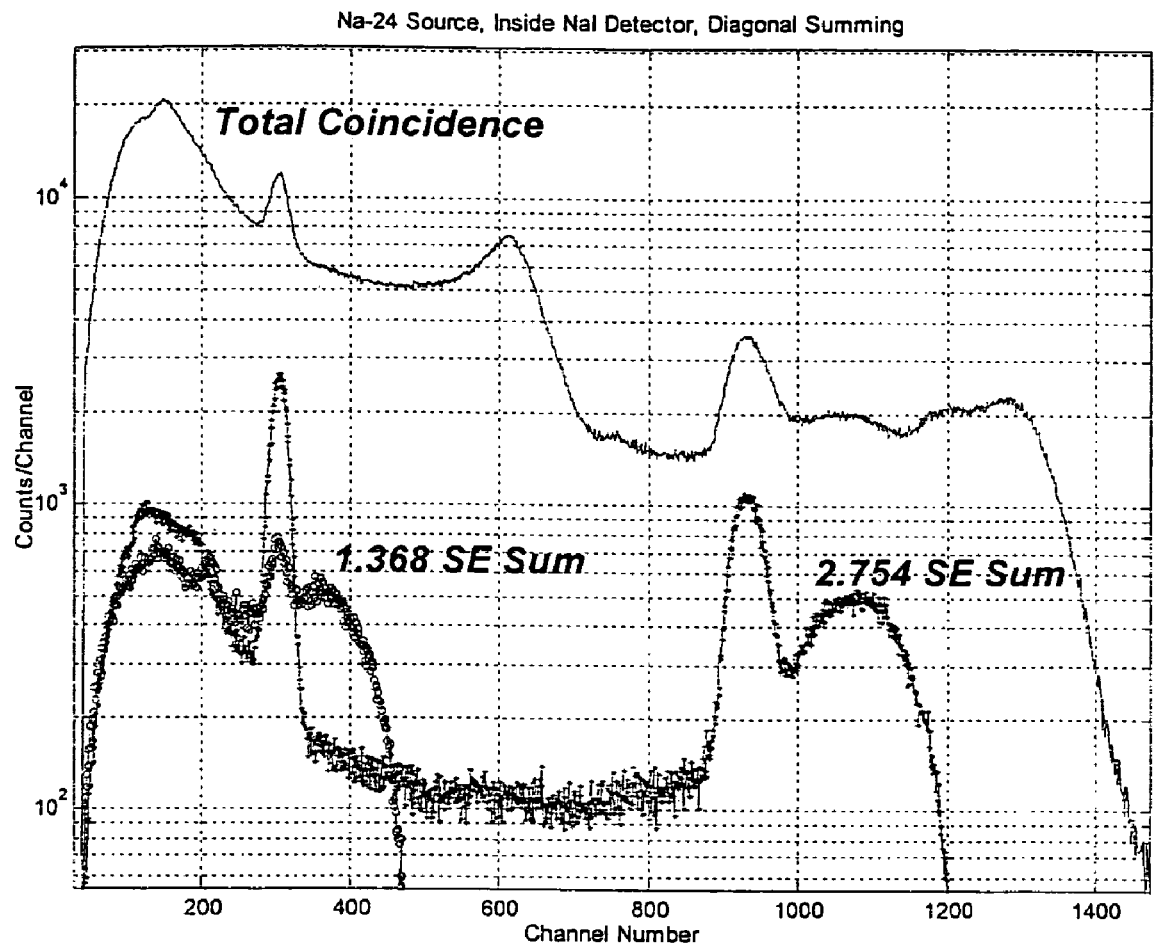
FIG. 11 is a graph illustrating a total coincidence spectrum, a coincidence summation spectrum at 1.368 MeV, and a coincidence summation spectrum at 2.754 MeV for a $^{24}$Na gamma ray source using diagonal summing techniques using an inner detector and corresponding to the single escapes of the 1.368 MeV and 2.754 MeV gamma rays according to embodiments of the present invention.
Figure 12:
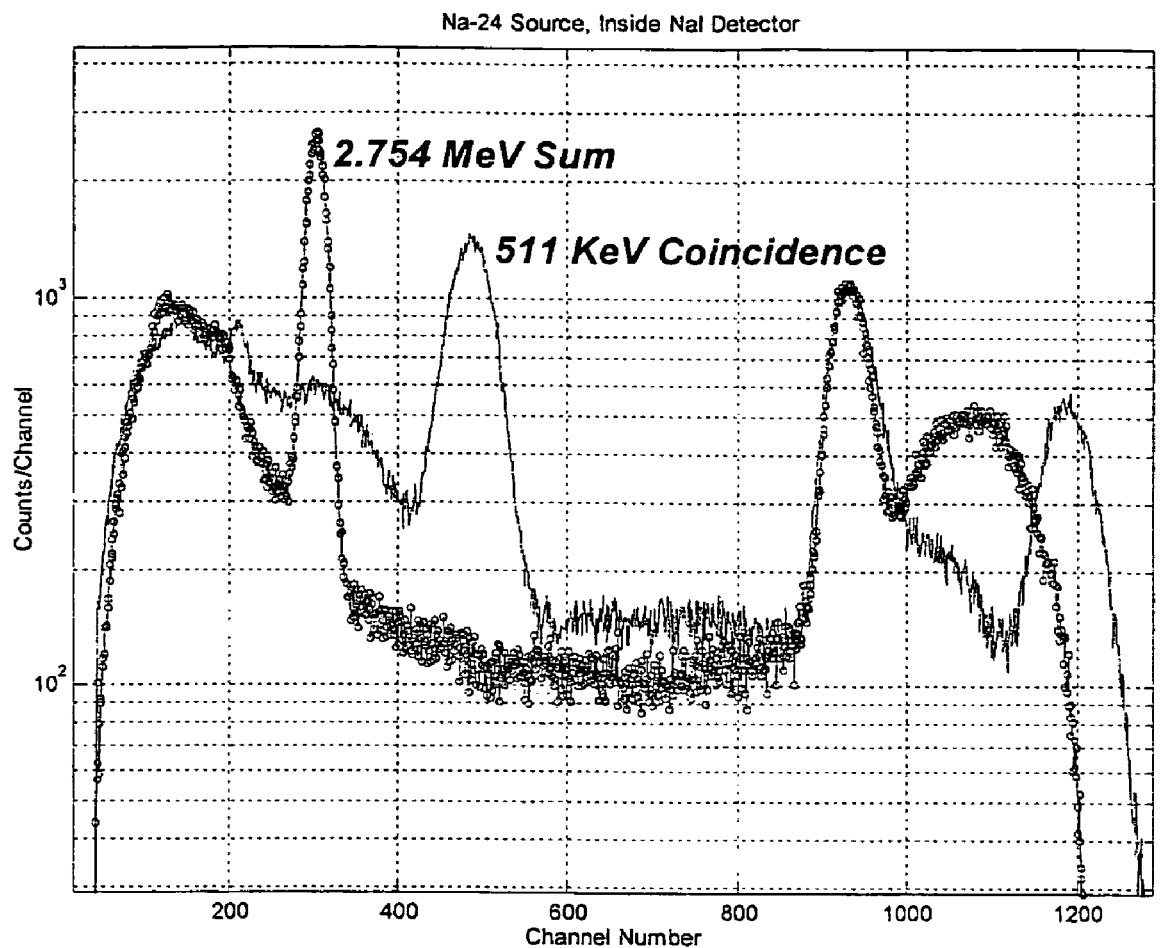
FIG. 12 is a graph illustrating a 0.511 MeV coincidence spectrum and a 2.754 MeV summation spectrum for a $^{24}$Na gamma ray source using an inner detector according to embodiments of the present invention.

FIG. 11 illustrates the two-dimensional diagonal summing spectra corresponding to the single escapes of the 1.368 MeV and 2.754 MeV gamma rays. The shape of the spectra can be described by the comments on the third and fifth features in Table 1. For comparison purposes, the 0.511 MeV coincidence spectrum and the 2.754 SE diagonal summing spectrum are shown in FIG. 11.

TABLE 1

Na-24 Two Dimensional Spectrum Features Using the New NaI Detector Arrangement

| # | Peaks Correspond to in the Well Detector | Inside Detector | Comment |
|---|---|---|---|
| [1] | Backscatter gamma | Compton Edge of the 2.754 MeV gamma ray | The spread around the peak is caused by the wide range of angles that the gamma ray can scatter through, not just 180 degrees |
| [2] | 0.511 MeV Annihilation gamma ray | Single escape of the 2.754 MeV gamma ray | Note how this feature and the first feature fall on the same diagonal line. This line corresponds to the 2.754 MeV sum. |
| [3] | Low energy gamma rays | High energy gamma rays, below the Compton Edge and above the double escape of the 2.754 MeV gamma ray | This feature lies on a diagonal line. This means that it corresponds to a certain energy sum, the double escape of the 2.754 MeV gamma ray. This feature is observed because of the partial energy deposition of the 0.511 MeV annihilation gamma ray in the inside detector before being completely detected by the Well detector |
| [4] | Low energy gamma rays | Double escape of the 2.754 MeV gamma ray | This feature is similar to the third feature except that there is no energy deposition in the inside detector by the 0.511 MeV annihilation gamma ray, only in the Well detector |
| [5] | 0.511 MeV Annihilation gamma ray | Double escape of the 2.754 MeV gamma ray | The diagonal line joining this feature and the third feature corresponds to the Single escape energy sum of the 2.754 MeV gamma ray. |
| [6] | Backscatter gamma | Compton Edge of the 1.368 MeV gamma ray | Same comment as first feature. |
| [7] | 0.511 MeV Annihilation gamma ray | Single escape of the 1.368 MeV gamma ray | Same comment as second feature, but for the 1.368 MeV gamma ray. |
| [8] | 0.511 MeV Annihilation gamma ray | Double escape of the 1.368 MeV gamma ray | Same comment as fifth feature, but for the 1.368 MeV gamma ray. |

Based on the different features in the two-dimensional spectrum of FIG. 8, various projections and resulting spectra can be obtained. The first projection is a vertical projection corresponding to the 0.511 MeV energy range in the outer "well" detector (such as detector 200 in FIG. 2B) and is shown in FIG. 9. For comparison, the single event and total The spectra extracted from the outer "well" detector (such as detector 200 in FIG. 2B) may be similar to those from the inner detector (such as detector 180 in FIG. 2B) for this energy range. These spectra may be less useful for the following reasons: 1. The outside "well" detector has a NaI base. This base may yield a higher light collection than the sides of the detector. This results in "Double Peaks" in the spectrum where each distinct gamma energy is represented by two peaks in the spectrum. 2. The detection efficiency of the outside "well" detector may be low for high energy gamma rays. This may be a consequence of the size of the outer "well" detector.

Figure 13:
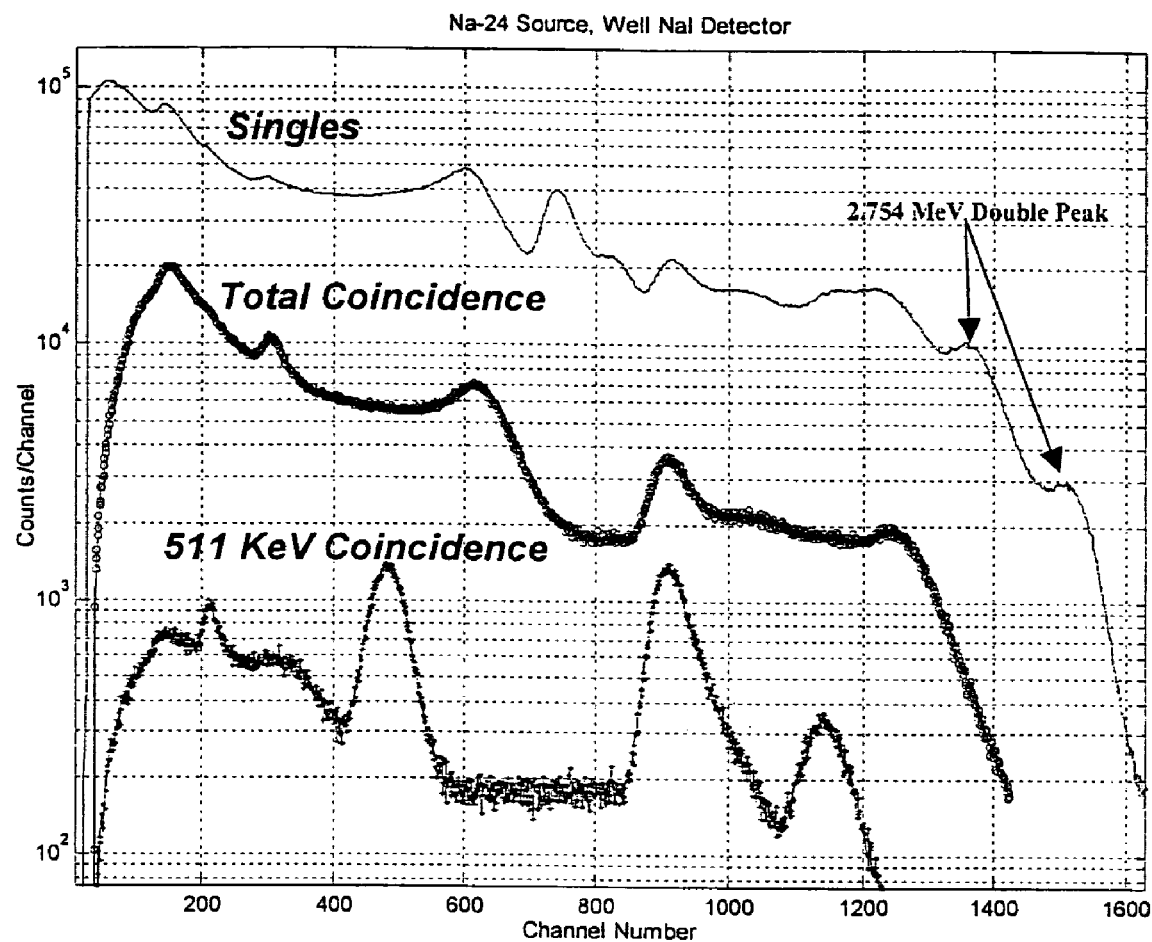
FIG. 13 is a graph illustrating a single events spectrum, a total coincidence spectrum, and a 0.511 MeV coincidence spectrum for a $^{24}$Na gamma ray source using an outer detector according to embodiments of the present invention.

Examples of the spectra obtained from the outer "well" detector are shown in FIG. 13. Two peaks that correspond to the 2.754 MeV gamma ray can be seen in the singles spectrum at approximately channels 1380 and 1510.

EXAMPLE 2

Sulfur Study

A natural sulfur sample was placed approximately 25 cm away from the center of a detector assembly, such as detector assembly 100 of FIG. 2B, in a thermal neutron beam produced by the PULSTAR educational reactor at North Carolina State University. The PULSTAR reactor is a 1 MW pool-type research reactor with 4% enriched, pin-type fuel consisting of uranium dioxide pellets in zircaloy cladding.

The main isotope in natural sulfur is $^{32}$S which, when activated by neutrons to $^{33*}$S, decays by emitting gamma rays with a wide energy range. A 5.4205 MeV gamma ray results from the decay of $^{33*}$S. The 5.4205 MeV gamma ray falls in the energy range of interest for oil well logging applications.

Figure 14:
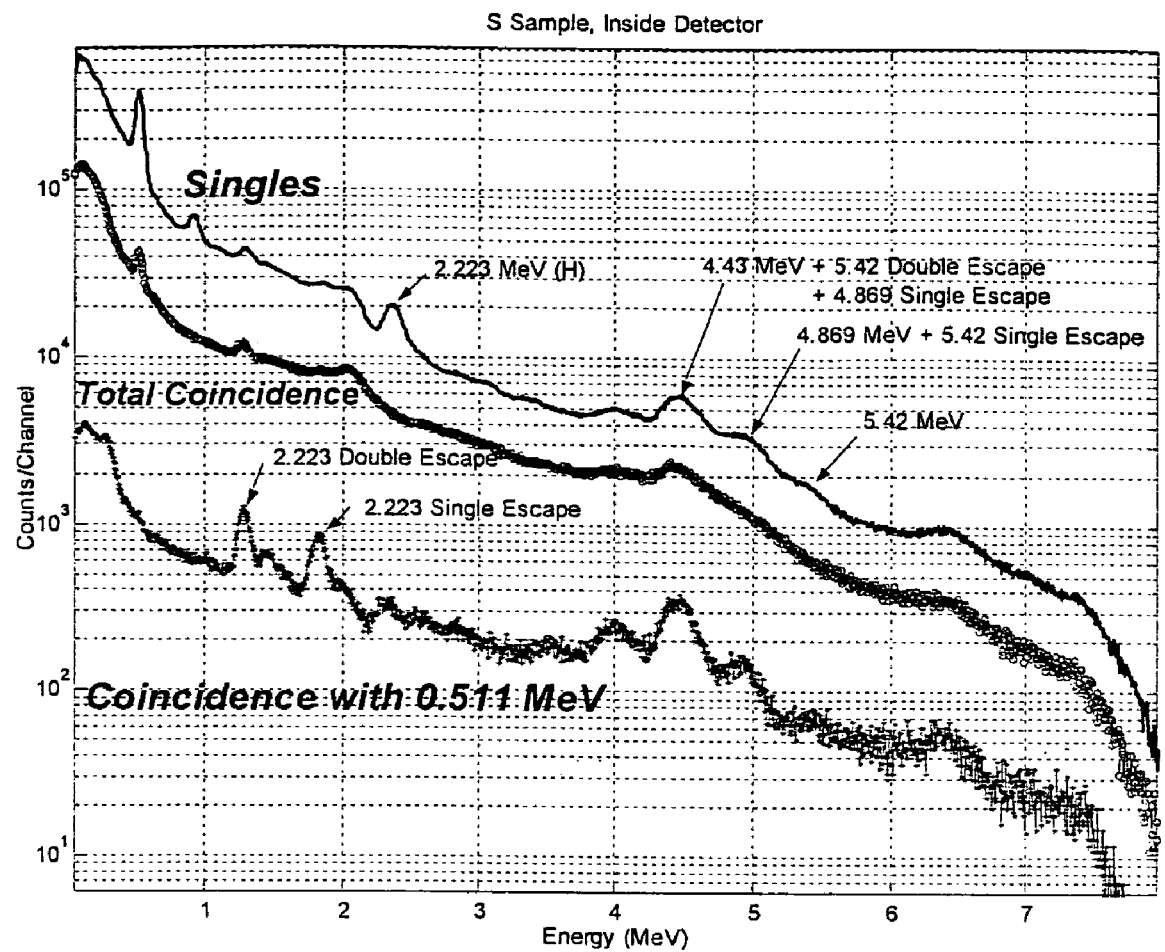
FIG. 14 is a graph illustrating a single events spectrum, a total coincidence spectrum, and a 0.511 MeV coincidence spectrum for a sulfur sample using an inner detector according to embodiments of the present invention.

FIG. 14 illustrates the singles, total coincidence, and 0.511 MeV coincidence spectra in the inside detector (such as detector 180 in FIG. 2B). The escape peaks of the 5.4205 MeV gamma ray are shown in the 0.511 MeV coincidence spectrum at 4.909 and 4.398 MeV. The escape peaks of the hydrogen 2.223 MeV gamma ray also show in the spectrum. This should not be a concern as this detector arrangement may also be used to detect higher energy gamma rays than the hydrogen gamma ray.

EXAMPLE 3

Yttrium

Figure 15:
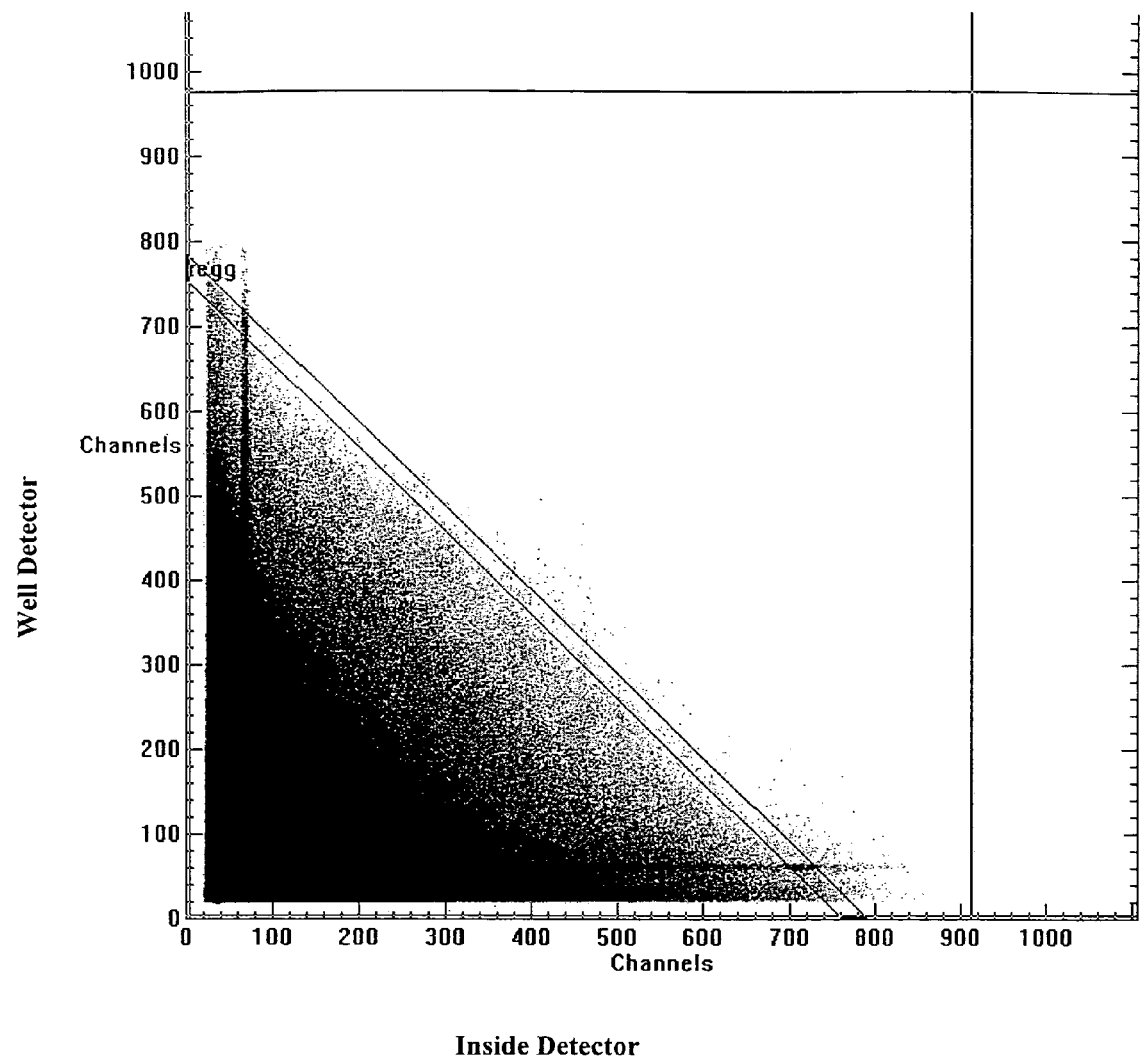
FIG. 15 is a graph illustrating a two-dimensional plot (flat view) of the counts in two NaI detectors for a Yttrium sample.
Figure 16:
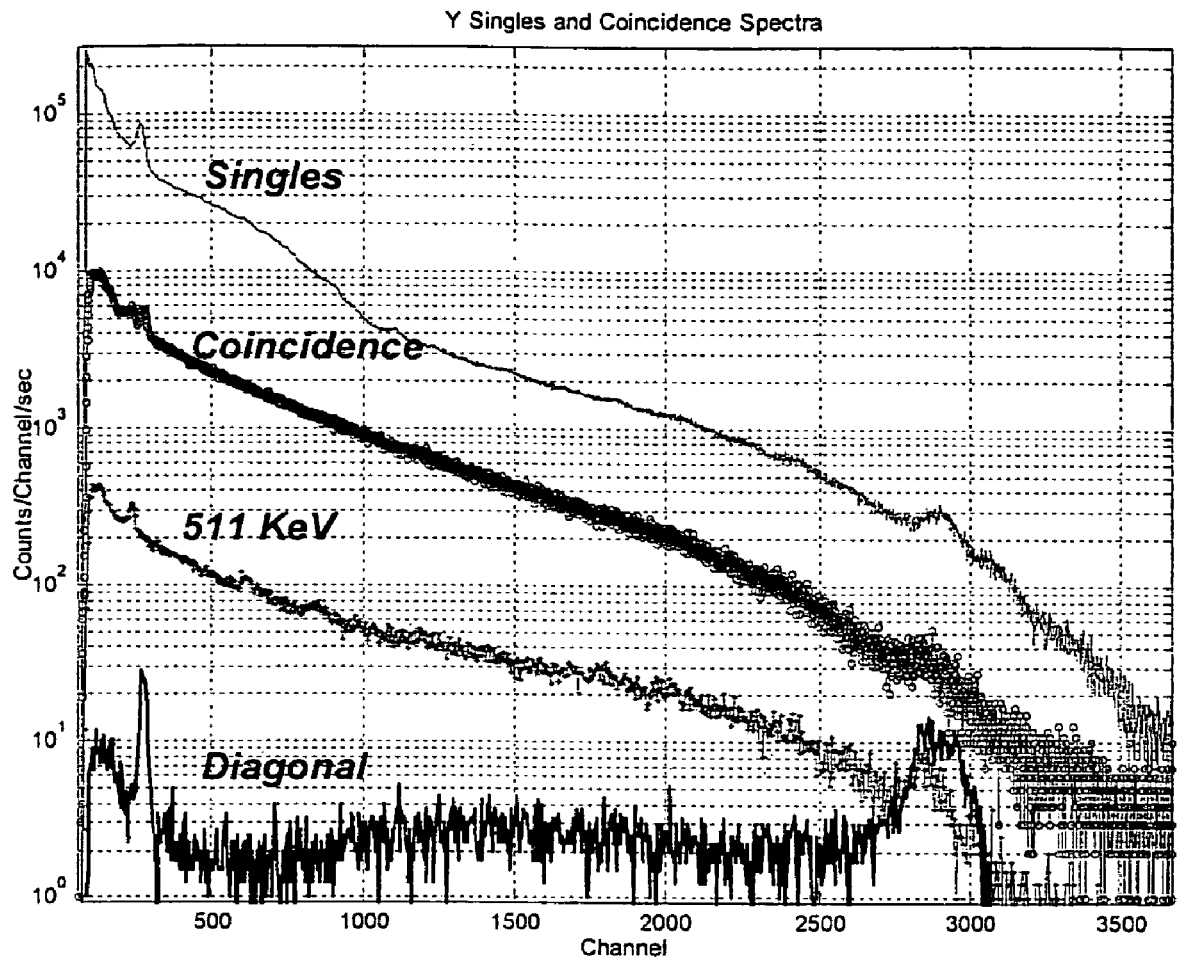
FIG. 16 is a graph illustrating a single events spectrum, a total coincidence spectrum, a 0.511 MeV coincidence spectrum, and a diagonal summation coincidence spectrum for a Yttrium sample according to embodiments of the present invention.

An yttrium sample was placed in a thermal neutron beam provided by the PULSTAR reactor. The sample was placed approximately 20 cm away from the center of a detector assembly, such as the detector assembly 100 shown in FIG. 2B, to simulate radiation in an oil well. FIG. 15 is a two-dimensional plot (flat view) of the event counts in both a NaI outside "well" detector (such as detector 200 in FIG. 2B) and the inside detectors (such as detector 180 in FIG. 2B). FIG. 16 illustrates a single detector, total coincidence, 0.511 MeV coincidence spectra, and the diagonal summing spectra that were obtained in the inside detector. The 0.511 MeV coincidence spectrum was obtained by extracting the spectrum from the two-dimensional array in the inside detector corresponding to the 0.511 MeV energy range in the outside "well" detector. The diagonal summing spectrum was obtained by projected the spectrum corresponding to the outlined diagonal energy window in FIG. 15 to the inside detector. The diagonal window corresponds to an energy of 6.079 MeV. This is the energy of the most intense gamma ray resulting from the capture of thermal neutrons by yttrium.

As illustrated in FIG. 16, the escape peaks of the 6.079 MeV gamma ray appear with a high signal-to-noise ratio in the 0.511 MeV coincidence and diagonal summing spectra as compared to the single detector and total coincidence spectra.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A gamma ray detector assembly for placement in a logging tool in a borehole, the detector assembly comprising:
    a first gamma ray detector elongated along an axis and defining a void extending along the axis;
    a second gamma ray detector conforming to at least a portion of the void, wherein the first and second gamma ray detectors are configured to be positioned in the borehole and to detect gamma ray events; and
    a signal processor configured to receive signals from the first and second gamma ray detectors and to graph the gamma ray events from the first and second gamma ray detectors as a function of energy in a two-dimensional representational plot to determine a rate of coincidence between a first event and a second event, wherein the first event and the second event sum to a predetermined energy between about 1.5 MeV and 11 MeV.

2. The detector assembly of claim 1, further comprising a substantially waterproof housing enclosing the first gamma ray detector and the second gamma ray detector.

3. The detector assembly of claim 1, wherein the first gamma ray detector and the second gamma ray detector are scintillation detectors.

4. The detector assembly of claim 3, further comprising a first photomultiplier tube in communication with the first gamma ray detector and a second photomultiplier tube in communication with the second gamma ray detector.

5. The detector assembly of claim 1, wherein the first and second gamma ray detectors are cylindrical, the first gamma ray detector forms an outer cylinder and the second gamma ray detector forms an inner cylinder.

6. The detector assembly of claim 1, wherein the first gamma ray detector has a variable thickness around the perimeter of the second gamma ray detector.

7. The detector assembly of claim 1, further comprising a shielding material on an end of the first gamma ray detector and a radioactive neutron source on a side of the shielding material facing away from the first gamma ray detector, wherein the radioactive source is configured to irradiate material in the borehole.

8. The detector assembly of claim 1, wherein the signal processor is configured to detect a first event in one of the first gamma ray detector and the second gamma ray detectors and to determine if a second event is detected in coincidence with the first event in the other of the first and the second gamma ray detectors.

9. The detector assembly of claim 1, wherein the signal processor is configured to determine the rate of coincidence between an event in one of the first and second gamma ray detectors and an annihilation photon in the other of the first and second gamma ray detectors.

10. The detector assembly of claim 1, wherein the signal processor is configured to determine the rate of coincidence between an event and two annihilation photons.

11. The detector assembly of claim 1, wherein the signal processor is further configured to determine a ratio of oxygen and carbon based on events in the first and second gamma ray detectors.

12. A method of detecting gamma rays in a borehole, the method comprising:
placing a first gamma ray detector and a second gamma ray detector into the borehole, wherein the first gamma ray detector is elongated along an axis and defines a void extending along the axis and the second gamma ray detector conforms to at least a portion of the void;
detecting a first event in one of the first gamma ray detector and the second gamma ray detector;
graphing the gamma ray events from the first and second gamma ray detectors as a function of energy to provide data in a two-dimensional representational plot;
determining whether a second event is detected in coincidence with the first event in the other of the first gamma ray detector and the second gamma ray detector; and
storing and/or providing to a user an indication of at least a portion of the data from the two-dimensional plot and/or determining step;
wherein determining whether a second event is detected in coincidence with the first event includes determining the rate of coincidence between a first event and a second event, and the first event and the second event sum to a predetermined energy between about 1.5 MeV and about 11 MeV.

13. The method of claim 12, wherein the first and second gamma ray detectors are cylindrical, wherein the first gamma ray detector forms an outer cylinder and the second gamma ray detector forms an inner cylinder.

14. The method of claim 12, wherein the first gamma ray detector has a thickness that varies around the perimeter of the second gamma ray detector.

15. The method of claim 12, further comprising: positioning a shielding material on an end of the first gamma ray detector; and positioning a radioactive source on a side of the shielding material facing away from the first gamma ray detector; and irradiating material in the borehole with the radioactive source.

16. The method of claim 12, further comprising providing a first photomultiplier tube in communication with the first gamma ray detector and a second photomultiplier tube in communication with the second gamma ray detector.

17. The method of claim 12, wherein determining whether a second event is detected in coincidence with the first event includes determining a rate of coincidence between an event in one of the first and second gamma ray detectors and an annihilation photon in the other of the first and second gamma ray detectors.

18. The method of claim 12, wherein determining whether a second event is detected in coincidence with the first event includes determining the rate of coincidence between an event and two annihilation photons.

19. The method of claim 12, further comprising determining a ratio of oxygen and carbon based on events in the first and second gamma ray detectors.

20. A method of detecting gamma rays in a borehole comprising:
placing a first gamma ray detector and a second gamma ray detector into the borehole;
detecting a first event in one of the first gamma ray detector and the second gamma ray detectors; and
graphing the gamma ray events from the first and second gamma ray detectors as a function of energy in a two-dimensional representational plot;
determining-whether a second event is detected in coincidence with the first event in the other of the first gamma ray detector and the second gamma ray detectors; and
storing and/or providing to a user an indication of at least a portion of the data from the two-dimensional plot and/or determining step, wherein the first event and the second event sum to a predetermined energy between about 1.5 MeV and about 11 MeV.

21. A method of detecting gamma rays in a borehole, the method comprising:
receiving gamma ray events emitted from materials adjacent a borehole, wherein the gamma ray events are detected by at least two gamma ray detectors; and
graphing gamma ray events from the at least two gamma ray detectors as a function of energy to provide data in a two-dimensional representational plot to determine whether two or more events are in coincidence with each other; and
storing and/or providing to a user an indication of at least a portion of the data from the two-dimensional plot.

* * * * *